United States Patent [19]

Dodge et al.

[11] Patent Number: 5,017,192
[45] Date of Patent: May 21, 1991

[54] FREE FLOW PREVENTION SYSTEM FOR INFUSION PUMP

[75] Inventors: Larry H. Dodge; Stanford C. Stone, both of St. Paul, Minn.

[73] Assignee: Minnesota Mining and Manufacturing Company, St. Paul, Minn.

[21] Appl. No.: 424,386

[22] Filed: Oct. 20, 1989

[51] Int. Cl.$^5$ .............................................. A61M 5/00
[52] U.S. Cl. ............................................ 604/250; 251/7
[58] Field of Search ............... 604/250, 246, 245, 34; 251/4.7; 137/637

[56] References Cited

U.S. PATENT DOCUMENTS

| | | | |
|---|---|---|---|
| 2,715,905 | 8/1955 | Ogle . | |
| 2,889,848 | 6/1959 | Redmer | 137/315 |
| 3,216,418 | 11/1965 | Scislowicz . | |
| 3,316,935 | 5/1967 | Kaiser et al. | 137/595 |
| 3,759,483 | 9/1973 | Baxter | 251/5 |
| 4,230,151 | 10/1980 | Jonsson | 137/595 |
| 4,236,880 | 12/1980 | Archibald | 417/478 |
| 4,261,388 | 4/1981 | Shelton | 137/486 |
| 4,277,226 | 7/1981 | Archibald | 417/38 |
| 4,322,201 | 3/1982 | Archibald | 417/279 |
| 4,434,963 | 3/1984 | Russell | 604/250 |
| 4,460,358 | 7/1984 | Somerville et al. | 604/250 |
| 4,519,792 | 5/1985 | Dawe | 604/152 |
| 4,527,588 | 7/1985 | Tseo et al. | 137/565 |
| 4,585,441 | 4/1986 | Archibald | 604/245 |
| 4,586,691 | 5/1986 | Kozlow | 251/7 |
| 4,620,564 | 11/1986 | Ekholmer | 137/595 |
| 4,689,043 | 8/1987 | Bisha | 604/250 |
| 4,818,190 | 4/1989 | Pelmulder et al. | 417/360 |

OTHER PUBLICATIONS

3M Flyer "AVI200A Infusion Pump: The Advanced Technology Volumetric Infusion Pump" IMED Corporation Brochure Gemini TM Administration Sets.

Primary Examiner—Stephen C. Pellegrino
Assistant Examiner—Ralph A. Lelois
Attorney, Agent, or Firm—Gary L. Griswold; Walter N. Kirn; Stephen W. Bauer

[57] ABSTRACT

A free flow prevention system for preventing free flow of fluid through IV tubing when the tubing is disconnected from an infusion pump. A flexible clamp is provided having a pair of clamping arms, which define a variable width slot for receiving the IV tubing. The IV tubing may be moved along the slot between a first position wherein the width of the slot is sufficient to permit the clamp to be positioned longitudinally along the IV tubing, and a second position wherein the width of the slot is normally less than the width of the slot at the first position. The clamping arms are resiliently biased to a closed position wherein the IV tubing is squeezed when in its second position to close the lumen to prevent fluid flow. A clamp-receiving passageway and clamp-opening wedge are provided on the infusion pump. The clamp-opening wedge is movable relative to a clamp received in the passageway to an operating position, wherein the wedge moves the arms of the flexible clamp against their bias to an open position wherein the lumen of the IV tubing is allowed to open to permit fluid flow during operation of the pump.

36 Claims, 3 Drawing Sheets

FREE FLOW PREVENTION SYSTEM FOR INFUSION PUMP

The invention relates generally to infusion pumps and IV tubing sets for the controlled delivery of fluids to a patient, and more particularly to a free flow prevention system for preventing free flow of fluid through the IV tubing when the tubing is disconnected from the infusion pump.

BACKGROUND OF THE INVENTION

Infusion pumps are typically used to regulate the delivery of fluids, which may include potentially hazardous drugs, to a patient with a high degree of accuracy. Ordinarily, a roller clamp is moved to a closed position to stop flow through IV tubing before the tubing is removed from an infusion pump in order to prevent a situation that is sometimes referred to as "free flow" or "fluid runaway", that is, where the fluid is free to flow rapidly through the IV tubing without regulation by the infusion pump. Such roller clamps are effective in preventing free flow only when they are manually moved to their closed positions, and free flow or fluid runaway may occur if the roller clamp is left in its open position. As a result, an automatic free flow prevention system is now desired wherein fluid runaway is prevented regardless of whether the pump operator remembers to close a roller or slide clamp.

One approach is described in co-assigned U.S. Pat. No. 4,585,441 wherein an interlock is provided to prevent removal of the IV set unless fluid flow through the tubing is stopped. The pump operator must manually close a clamp to stop fluid flow through the tubing before the infusion pump will permit removal of the IV set.

Another approach is to provide a permanent clamp on the infusion pump itself from which the IV set must be manually disconnected during removal of the IV set from the infusion pump. That approach reduces the risk of fluid runaway because the permanent clamp reduces the possibility of thoughtless removal of the IV set from the infusion pump. The act of disconnecting the IV set from the permanent clamp tends to remind the operator of the need to close the roller or slide clamp on the IV set; however, it does not eliminate the risk that the operator will remove the IV set without closing a clamp.

Other approaches include employing slide clamps to prevent or reduce the risk of removing the IV set without closing a clamp. U.S. Pat. Nos. 4,586,691; 4,689,043 and 4,818,190 describe employing slide clamps to prevent fluid runaway during removal of IV sets from infusion pumps.

SUMMARY OF THE INVENTION

The invention provides a free flow prevention system adapted for preventing free flow of fluid through IV tubing when the tubing is disconnected from an infusion pump. The system is designed to be easy to use, and to automatically close the IV tubing to fluid flow when the tubing is disconnected from the infusion pump.

Generally, the free flow prevention system comprises IV tubing having a lumen through which fluid may be pumped for administration to a patient, and a flexible clamp associated with the IV tubing. A pumping assembly is provided that includes pumping means for pumping fluid through the IV tubing, and releasable holding means for holding the IV tubing during operation of the pumping assembly.

The flexible clamp has a pair of clamping arms defining a variable width slot along which the IV tubing may be moved between a first position wherein the width of the slot is sufficient to permit the clamp to be positioned longitudinally along the IV tubing, and a second position wherein the width of the slot is normally less than the width of the slot at the first position. The clamping arms are resiliently biased to a closed position wherein the IV tubing is squeezed when in its second position to close the lumen to prevent fluid flow, and are movable against the bias to an open position wherein the lumen of the IV tubing is allowed to open so that flow through the lumen is permitted.

Clamp-receiving means are provided on the pumping assembly for releasably receiving the flexible clamp, and releasable clamp-opening means are provided for separating the clamping arms of the flexible clamp and moving the arms from their closed position to the open position before operation of the pumping assembly. The clamp-receiving means and clamp-opening means are mounted on the pumping assembly for movement of the clamp-opening means relative to the flexible clamp received in the clamp-receiving means between an unloading position and an operating position. In the unloading position, the clamp-opening means does not hold the arms of the flexible clamp in their open position. In the operating position, the clamp-opening means moves the arms of the flexible clamp to their open position and holds the arms in the open position.

Other features will be in part apparent and in part pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION

Figure 1:
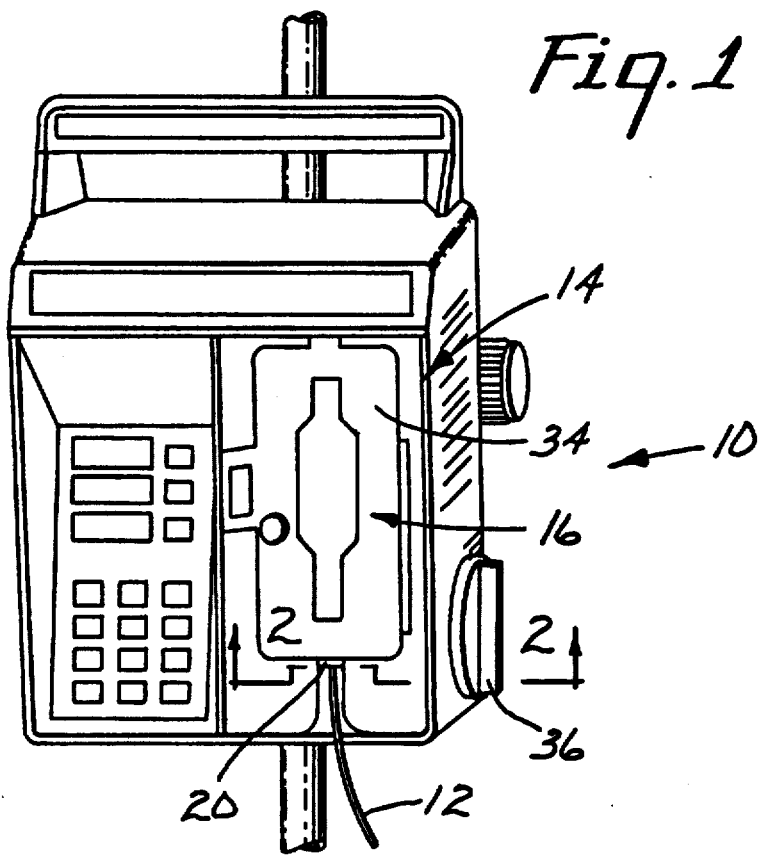
FIG. 1 is a perspective view of an infusion pump incorporating the free flow prevention system of the invention.

The infusion pump designated in its entirety by the reference numeral 10 in FIG. 1 may be of the general type described in U.S. Pat. Nos. 4,236,880; 4,277,226 and 4,322,201 (incorporated herein by reference). Such infusion pumps are designed for use with IV tubing 12 that includes a pumping cassette having flexible walls defining fluid pumping chambers which may be compressed to regulate fluid flow through the IV tubing 12. Infusion pumps of this type are being sold by AVI, Inc., a subsidiary of Minnesota Mining and Manufacturing Company of St. Paul, Minn., under the various trade designations of the "AVI 200" and "AVI 400" model series infusion pumps. The infusion pump 10 may alternatively be of the type commonly referred to as a "linear peristaltic pump", that is, pumps that selectively squeeze straight portions of the IV tubing to regulate or pump fluid through the IV tubing. In any event, the infusion pump 10 regulates fluid flow through the lumen of IV tubing 12 for administration to a patient.

The infusion pump 10 includes a pumping assembly shown generally at 14 employing conventional pumping means for pumping fluid through the IV tubing 12, and a releasable holding means or assembly 16 for holding the IV tubing 12 during operation of the pumping assembly 14. Clamp-receiving means, such as the walls forming an elongate passageway 18 having an open end 19, are provided on the releasable holding means 16 of the pumping assembly 14 for releasably receiving a flexible clamp 20 associated with the IV tubing 12. And releasable clamp-opening means 22 are provided for separating the clamping arms 24 of the flexible clamp 20 and moving the arms 24 from their closed position (FIG. 2) to the open position (FIG. 3) before operation of the pumping assembly 14 so that fluid can flow through the IV tubing 12.

Figure 2:
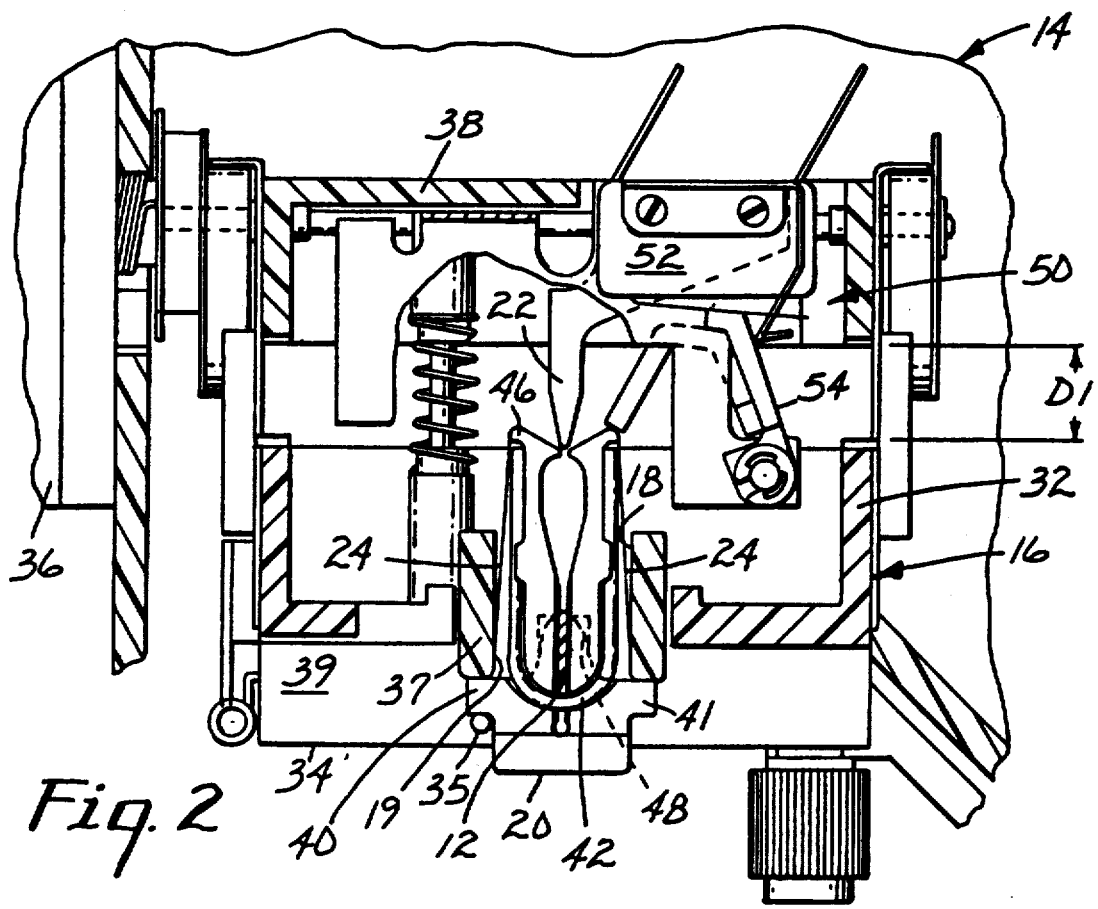
FIG. 2 is a cross-sectional view substantially along line 2—2 of FIG. 1, showing a flexible clamp of the free flow prevention system in its closed position.
Figure 3:
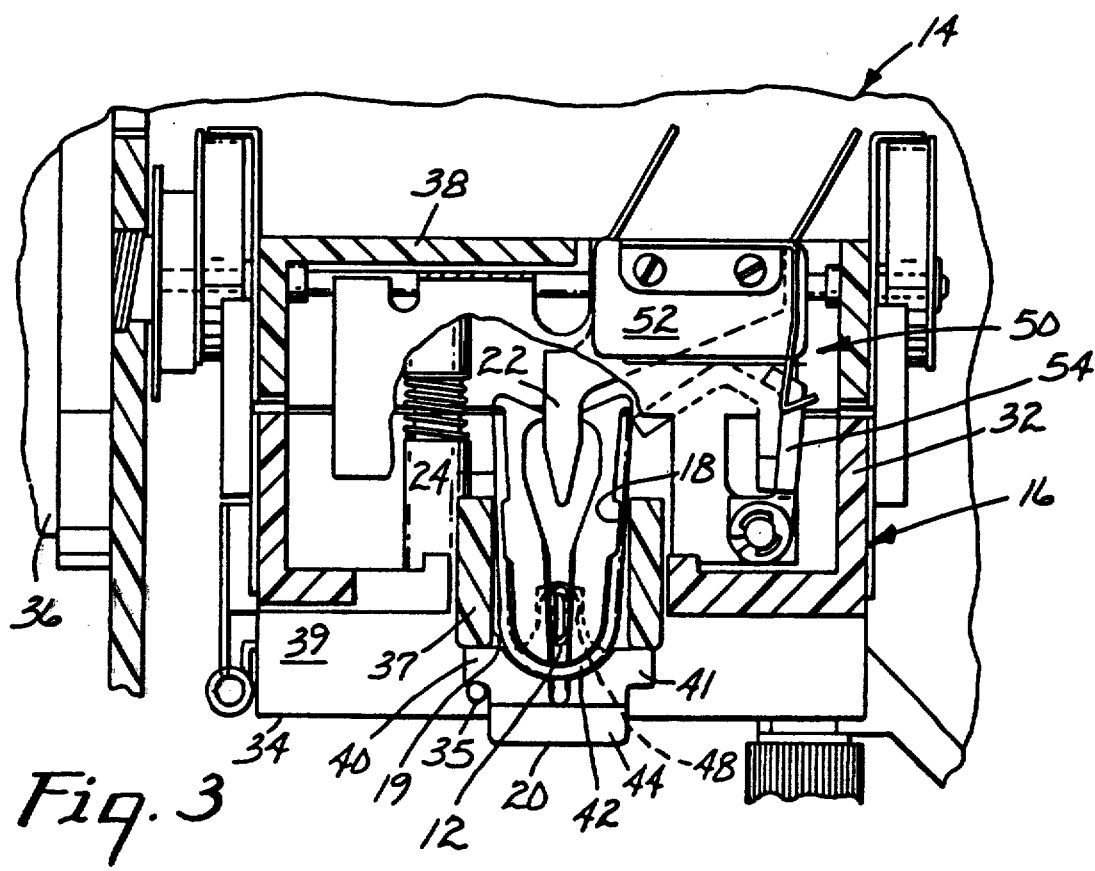
FIG. 3 is a cross-sectional view similar to FIG. 2, showing the flexible clamp in its open position.

The clamp-receiving means 18 and clamp-opening means 22 are mounted on the infusion pump 10 for movement of the clamp-opening means 22 relative to a flexible clamp 20 received in the clamp-receiving means 18 between an unloading position (FIG. 2) and an operating position (FIG. 3). In the unloading position (FIG. 2), the clamp-opening means 22 does not hold the arms 24 of the flexible clamp 20 in their open position so that flow through the lumen of the IV tubing 12 is prevented before unloading the IV tubing set from the infusion pump 10. When the clamp-receiving means 18 and clamp-opening means 22 are moved from the unloading position to the operating position (FIG. 3), the clamp-opening means 22 moves the arms 24 of the flexible clamp 20 to their open position and holds the arms 24 in the open position.

The flexible clamp 20 (FIG. 4) includes at least a pair of the clamping arms 24, which define a variable width slot 26. The IV tubing 12 may be moved along the slot 26 between a first position 28 (FIG. 4) wherein the width of the slot 26 is sufficient to permit the clamp 20 to be positioned longitudinally along the IV tubing 12, and a second position 30 wherein the width of the slot 26 is normally less than the width of the slot 26 at the first position. The clamping arms 24 are resiliently biased to a closed position (FIGS. 2 and 4) wherein the IV tubing 12 is squeezed when in its second position 30 (FIG. 2) to close the lumen to prevent fluid flow. The clamping arms 24 are movable against the bias to an open position (FIG. 3) wherein the lumen of the IV tubing 12 is allowed to open so that flow through the lumen is permitted.

As shown in FIGS. 2 and 3, the releasable holding means 16 is preferably in the form of a door assembly 16 including an IV pumping cassette-receiving block 32 of the type described in co-assigned U.S. Pat. No. 4,236,880, and a door 34 pivotably mounted on the cassette-receiving block 32 by a hinge. As described in the co-assigned U.S. patent, the door assembly 16 may be manually moved between a loading and unloading position (FIG. 2) and an operating position (FIG. 3) by turning a knob 36 extending laterally outwardly from a side of the infusion pump 10. In the loading and unloading position (FIG. 2), the door assembly 16 is spaced from the main body 38 of the infusion pump 10 a distance D-1 sufficient to permit the door 34 to be pivoted outwardly for loading and unloading the pumping cassette of the IV tubing 12. When the door assembly 16 is moved to the operating position (FIG. 3), the door assembly 16 is moved toward the main body 38 of the infusion pump 10 to bring the pumping cassette into position for proper operation of the pistons of the pumping means.

The clamp-opening means 22 preferably includes a wedge 22 mounted on the main body 38 of the pumping assembly 14, and the clamp-receiving passageway 18 is preferably formed in the cassette-receiving block 32 of the door assembly 16. For example, a guide block 37 may be provided on the cassette-receiving block 32 to form the passageway 18. When the door assembly 16 is in its loading and unloading position (FIG. 2), the IV tubing 12 may be loaded into or unloaded from the pumping assembly 14, and the wedge 22 and flexible clamp 20 are in their unloading position after the clamp 20 is fully inserted in the clamp-receiving passageway 18. And when the door assembly 16 is moved to the operating position (FIG. 3), the flexible clamp 20 is carried along in the clamp-receiving passageway 18 toward the wedge 22 to the operating position, with at least a portion the wedge 22 positioned between the clamping arms of the flexible clamp to move the clamping arms 24 to their open position.

A projecting portion or pin 35 preferably extends downwardly from the bottom edge 39 of the door 34. The pin 35 is adapted for releasably retaining the flexible clamp 20 in the elongate passageway 18 after the clamp 20 is manually inserted in the passageway 18 and the door 34 is closed against the cassette-receiving block 32. It will be observed that the pin 35 does not prevent removal of the clamp 20 when the door 34 is open. The pin 35 engages a ledge 40 extending laterally outwardly from the inner end of one of the clamping arms 24 to hold the clamp 20 against longitudinal movement (downwardly in FIGS. 2 and 3) when the wedge 22 separates the clamping arms 24 of the clamp 20.

The flexible clamp 20 preferably comprises a body formed of thermoplastic or synthetic resin material, and a resilient spring member 42 biasing the clamping arms 24 to their closed position (FIG. 2). The body of the flexible clamp 20 includes a hinged bridging portion 44 defining an inner end of the slot 26, and the clamping arms 24. The clamping arms 24 of the clamp 20 extend outwardly (upwardly in FIG. 4) from the bridging portion 44, and terminate in free ends 46 that define the outer end of the slot 26. The free ends 46 of the clamping arms 24 are tapered inwardly toward the slot 26 and bridging portion 42 to guide the wedge 22 into the outer end of the slot 26 between the clamping arms 24.

Figure 4:
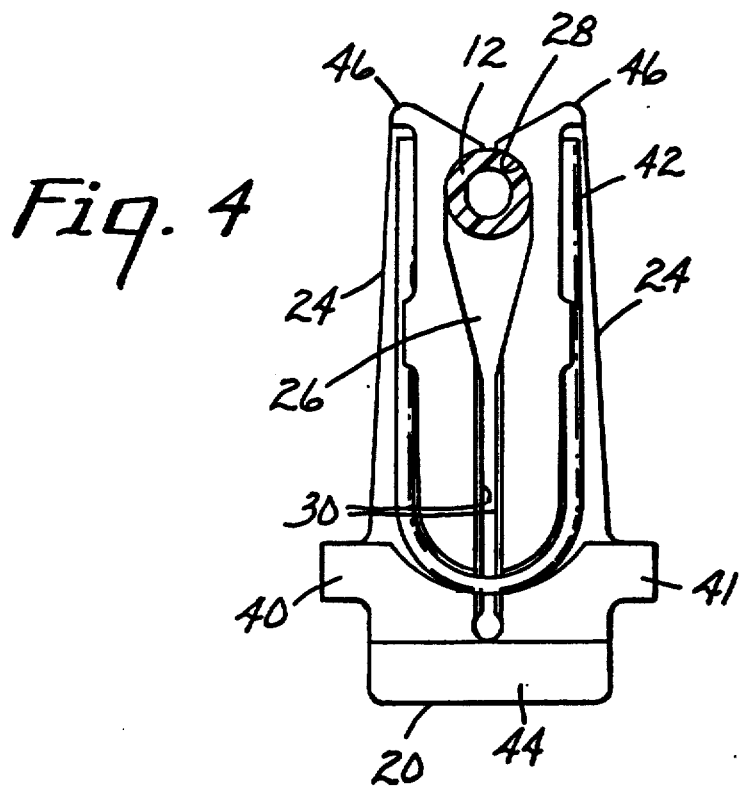
FIG. 4 is an enlarged bottom plan view of the flexible clamp of FIGS. 2 and 3.

The clamping arms 24 have inner surface portions between the inner end of the slot 26 and their free ends 46, preferably generally adjacent their free ends, that define the first (wide) position 28. And the inner end of the slot 26 may be, for example, generally adjacent the second position 30 as shown in FIGS. 2-4, with a portion of the clamping arms 24 generally adjacent the bridging portion 44 defining an open area as the second (narrow) position. The slot 26 defines the longitudinal direction or axis of the clamp 20.

Abutment means, such as ledges 40 and 41 extending laterally outwardly from opposite sides of the clamp 20, may be provided on the clamp 20. The ledges 40 and 41 limit insertion of the clamp 20 into the elongate passageway 18 to a first predetermined distance, with the first and second positions 28 and 30 of the IV tubing 12 being spaced apart along the longitudinal axis of the clamp 12 a second predetermined distance substantially equal to the first predetermined distance. In other words, the ledges 40 and 41 are preferably spaced from the free ends 46 of the clamping legs 24 distance substantially equal to the distance separating the first and second positions 28 and 30. And the cassette-receiving block 32 of the pumping assembly 14 includes a wall 48 substantially preventing movement of the IV tubing 20 into the passageway 18 as the clamp 20 is inserted into the passageway 18 so that the IV tubing 18 is moved from the first position 28 to the second position 30 when the clamp 20 is manually inserted in the passageway 18 the first predetermined distance.

A sensor 50 (FIGS. 2 and 3) may be provided to determine when the clamp 20 is fully inserted in passageway 18, and the infusion pump 10 may include alarm circuitry responsive to the sensor 50, and may even be electrically disabled when the sensor 50 fails to indicate a fully inserted clamp 20. The sensor 50 includes a proximity switch 52 and a suitable linkage 54 for tripping the proximity switch 52 when the clamp 20 is fully inserted.

Figure 5:
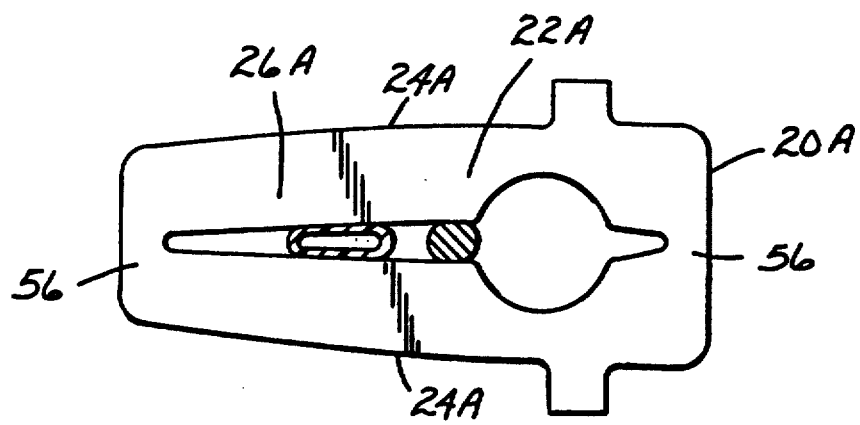
FIG. 5 is a bottom plan view similar to FIG. 4, illustrating another embodiment of the flexible clamp.

FIG. 5 illustrates a second embodiment of a flexible clamp 20A, which includes two bridging portions 56 joining the clamping arms 24A and defining opposite ends of the variable width slot 26A. The bridging portions 56 and/or clamping arms 24A are sufficiently flexible to permit the clamping arms 24A to be moved against the bias to their open position (FIG. 5) despite the addition of a second bridging portion 56. FIG. 5 also illustrates how a clamp-opening wedge 22A may be used with this alternative design. The wedge 22A would be driven into the slot 26A in the transverse direction (i.e., perpendicular to the sheet of the drawing in FIG. 5) to separate the clamping arms 24A.

Figure 6:
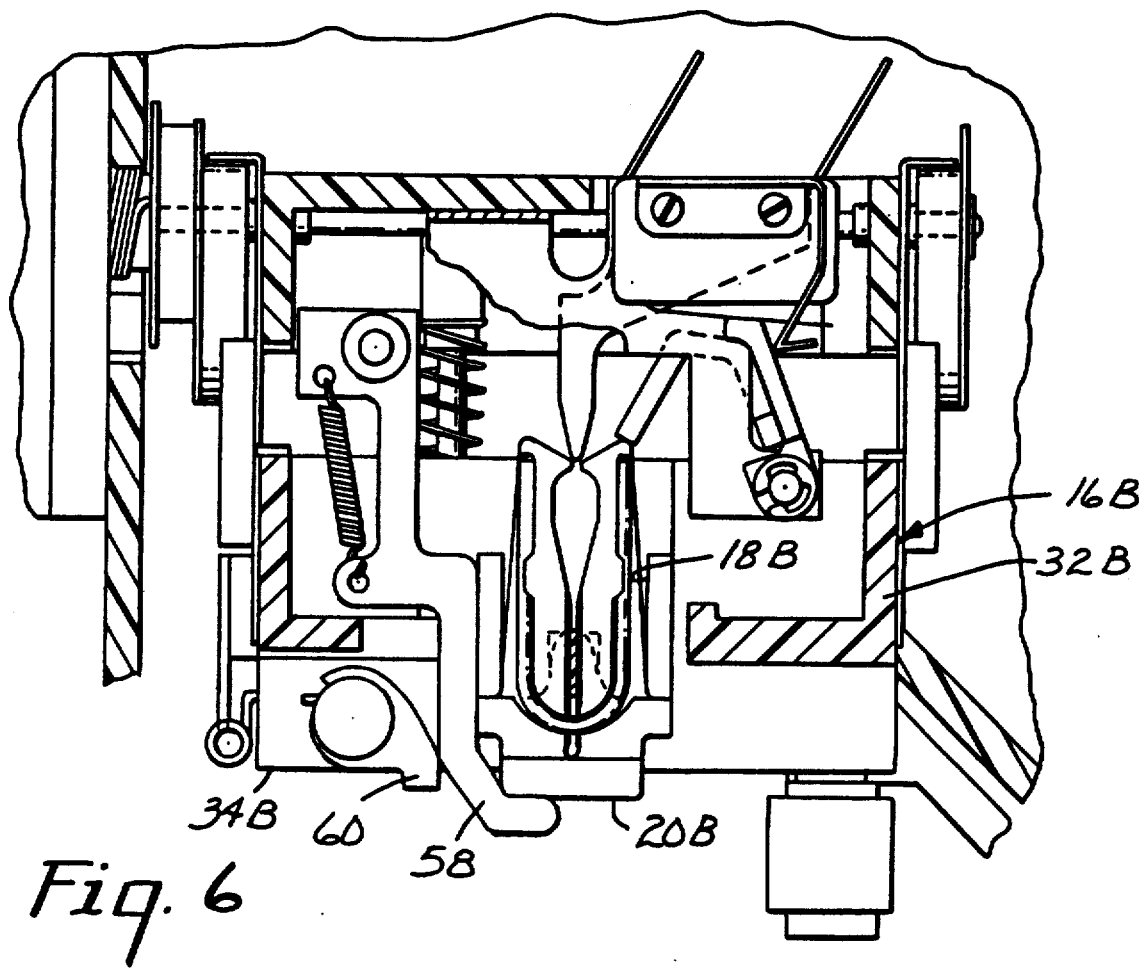
FIG. 6 is a cross-sectional view similar to FIGS. 2 and 3 showing a second embodiment of a clamp-receiving mechanism of the invention.

FIG. 6 illustrates another embodiment of the free flow prevention system wherein a pivotable arm 58 is provided for releasably retaining the flexible clamp 20B in the passageway 18B when the clamp 20B is inserted the first predetermined distance. The pivotable arm 58 is preferably pivotably mounted on the cassette-receiving block 32B so that the arm 58 moves with the door assembly 16B. The door 34B has a pivotable projecting portion 60 spring biased to a holding position (FIG. 6) for pressing or holding the pivotable arm 58 against the clamp 20B when the door 34B is moved to a closed position. And the projecting portion 60 is movable against the spring bias by the pivotable arm 58 when the clamp 20B is partially inserted in the passageway 18B and the door 34B is closed. This ability to move against the spring bias is believed to prevent jamming of the door 34B when the clamp 20B is only partially inserted in the passageway 18B.

The operation of the free flow prevention system will be described with respect to the embodiment shown in FIGS. 2-4. With the IV tubing 12 at the first (wide) position 28 in the slot 26, the clamp 20 is moved longitudinally along the tubing 12 to a position appropriate for insertion of both the tubing 12 and clamp 20 into the infusion pump 10. The IV tubing 12, including the pumping cassette, if any, and the clamp 20 are then manually placed or inserted into the cassette-receiving block 32 and the clamp-receiving passageway 18, with the IV tubing 12 moving to the second position 30 in the clamp's slot 26 as the clamp 20 is inserted. The door 34 of the door assembly 16 is then closed to hold the clamp 20, cassette and IV tubing 12 in the door assembly 16, and the knob 36 is turned to pull the door assembly 16 toward the main body 38 of the pumping assembly 14. As the door assembly 16 moves toward the main body 38 of the pumping assembly 14, the wedge 22 is forced between the clamping arms 24 of the clamp 20 to move them to the open position (FIG. 3) to permit fluid flow through the IV tubing 12 during operation of the pump 10.

In order to remove the IV tubing set from the pump 10, the knob 36 is turned in the opposite direction to return the door assembly 16 to its loading and unloading position (FIG. 2), where it is spaced from the main body 38 of the pumping assembly 14. The door 34 is then opened, and the IV tubing set, including the IV tubing 12 and clamp 20, are removed from the infusion pump 20, with the the lumen of the IV tubing 12 being closed due to the clamping action of the clamping arms 24 against the tubing 12 at the second position 28. As a result, free flow through the tubing 12 is prevented during and after disconnection of the IV tubing set regardless of whether a standard roller clamp (not shown) is closed.

As various changes could be made in the above constructions without departing from the scope of the invention, it is intended that all matter contained in the above description or shown in the accompanying drawing be interpreted as illustrative and not in a limiting sense.

We claim:
1. A free flow prevention system comprising:
   IV tubing having a lumen through which fluid may be pumped for administration to a patient;
   a pumping assembly including pumping means for pumping fluid through the IV tubing, and releasable holding means for holding the IV tubing during operation of the pumping assembly;
   a flexible clamp associated with the IV tubing and having a pair of clamping arms defining a variable width slot along which the IV tubing may be moved between a first position wherein the width of the slot is sufficient to permit the clamp to be positioned longitudinally along the IV tubing, and a second position wherein the width of the slot is normally less than the width of the slot at the first position, the clamping arms being resiliently biased to a closed position wherein the IV tubing is squeezed when in its second position to close the lumen to prevent fluid flow, the clamping arms being movable against the bias to an open position wherein the lumen of the IV tubing is allowed to open so that flow through the lumen is permitted;
   clamp-receiving means on the pumping assembly for releasably receiving the flexible clamp; and
   releasable clamp-opening means for separating the clamping arms of the flexible clamp and moving the arms from their closed position to the open position before operation of the pumping assembly;
   the clamp-receiving means and clamp-opening means being mounted on the infusion pump for movement of the clamp-opening means relative to the flexible clamp received in the clamp-receiving means between an unloading position, wherein the clamp-opening means does not hold the arms of the flexible clamp in their open position, and an operating position, wherein the clamp-opening means moves the arms of the flexible clamp to their open position and holds the arms in the open position.

2. A free flow prevention system according to claim 1 wherein the clamp-opening means includes a wedge mounted on the pumping assembly for separating the clamping arms of the flexible clamp, the wedge and the flexible clamp being movable relative to one another between the operating position, wherein at least a portion of the wedge is positioned between the clamping arms to separate and hold the arms in their open position, and the unloading position, wherein the wedge is not opening the clamping arms from their closed position so that the lumen of the IV tubing is closed to fluid flow when the IV tubing is removed from the pumping assembly.

3. A free flow prevention system according to claim 2 wherein the clamp-receiving means is mounted or formed on the releasable holding means, and the releasable holding means is movable between a loading and unloading position, wherein the IV tubing may be loaded into or unloaded from the pumping assembly and the wedge and flexible clamp are in their unloading position, and the operating position wherein the flexible clamp is moved to the operating position relative to the wedge and the clamp and IV tubing are held for operation of the pumping assembly.

4. A free flow prevention system according to claim 2 wherein the flexible clamp has a bridging portion defining an inner end of the slot, the clamping arms of the clamp extending outwardly from the bridging portion and terminating in free ends that define the outer end of the slot, the free ends of the arms being tapered inwardly toward the slot and bridging portion to guide the wedge into the outer end of the slot between the clamping arms.

5. A free flow prevention system according to claim 4 wherein the clamping arms define a portion of the slot generally adjacent the inner end of the slot as the second position having a width normally less than the width of the slot at the first position, and the clamping arms have portions generally adjacent their free ends that define an open area generally adjacent the free ends as the first position wherein the width of the slot is sufficient to permit the clamp to move longitudinally along the IV tubing.

6. A free flow prevention system according to claim 5 wherein the flexible clamp comprises a body formed of thermoplastic or synthetic resin material, and a resilient spring member biasing the clamping arms to their closed position.

7. A free flow prevention system according to claim 1 wherein the clamp-receiving means comprise walls in the releasable holding means defining an elongate passageway having an open end for receiving the flexible clamp, the releasable holding means being movable between a loading and unloading position, wherein the IV tubing may be loaded into and unloaded from the pumping assembly, and an operating position, wherein the IV tubing is held for operation of the pumping assembly, the clamp-opening means being positioned in the elongate passageway such that the clamping arms are moved from their closed position to their open position when the releasable holding means is moved to the operating position.

8. A free flow prevention system according to claim 7 further comprising abutment means on the clamp for limiting insertion of the clamp into the elongate passageway to a first predetermined distance, the slot of the flexible clamp defining a longitudinal axis of the clamp, with the first and second positions of the IV tubing being spaced apart along the longitudinal axis of the clamp a second predetermined distance substantially equal to the first predetermined distance, the pumping assembly including a wall substantially preventing movement of the IV tubing into the elongate passageway as the flexible clamp is inserted into the elongate passageway so that the IV tubing is moved from the first to the second positions when the flexible clamp is inserted in the elongate passageway the first predetermined distance.

9. A free flow prevention system according to claim 8 wherein the clamp-receiving means includes a pivotable arm for releasably retaining the flexible clamp in the passageway when the clamp is inserted the first predetermined distance.

10. A free flow prevention system according to claim 9 wherein the releasable holding means of the pumping assembly includes a door having a pivotable projecting portion spring biased to a holding position for pressing or holding the arm against the flexible clamp when the door is moved to a closed position, the projecting portion being movable against the spring bias by the pivotable arm when the clamp is partially inserted in the passageway and the door is closed to prevent jamming of the door when the clamp is only partially inserted in the passageway.

11. A free flow prevention system according to claim 10 wherein the IV tubing includes a pumping cassette having flexible walls defining fluid pumping chambers that may be compressed by the pumping means to regulate fluid flow through the IV tubing, the door of the pumping assembly being adapted to hold the pumping cassette in the pumping assembly.

12. A free flow prevention system according to claim 10 wherein the flexible clamp includes two bridging portions joining the clamping arms and defining opposite ends of the variable width slot, the bridging portions and/or clamping arms being sufficiently flexible to permit the clamping arms to be moved against the bias to their open position.

13. A free flow prevention system according to claim 8 wherein the releasable clamp-opening means includes a wedge on the pumping assembly that separates the clamping arms of the flexible clamp when the releasable holding means of the pumping assembly is moved to its operating position such that the arms are held in their open position, the releasable holding means of the pumping assembly including a door having a projecting portion adapted for releasably retaining the flexible clamp in the elongate passageway when the clamp is inserted the first predetermined distance and the door is moved to a closed position whereby the flexible clamp is held against longitudinal movement by the projecting portion when the wedge separates the clamping arms of the flexible clamp.

14. An infusion pump for regulating fluid flow through a lumen of IV tubing to a patient and being adapted for use with a flexible clamp that prevents free flow of the fluid through the IV tubing after the tubing is disconnected from the infusion pump, the clamp being of the type having a pair of clamping arms defining a variable width slot along which the IV tubing may be moved between a first position wherein the width of the slot is sufficient to permit the clamp to be positioned longitudinally along the IV tubing, and a second position wherein the width of the slot is normally less than the width at the first position, the clamping arms being resiliently biased to a closed position wherein the IV tubing is squeezed when in the second position to close the lumen to prevent fluid flow, the clamping arms being movable against the bias to an open position wherein the lumen of the IV tubing is allowed to open so that flow through the lumen is permitted; the infusion pump comprising:
- a pumping assembly including pumping means adapted for pumping fluid through the IV tubing, and releasable holding means adapted for holding the IV tubing during operation of the pumping assembly;
- clamp-receiving means on the pumping assembly adapted for releasably receiving the flexible clamp; and
- releasable clamp-opening means adapted for separating the clamping arms of the flexible clamp and moving the arms from their closed position to the open position before operation of the infusion pump;
- the clamp-receiving means and clamp-opening means being mounted on the infusion pump for movement relative to one another between an unloading position, wherein the clamp-opening means does not hold the arms of a flexible clamp received in the clamp-receiving means in their open position, and an operating position wherein the clamp-opening means moves the arms of a flexible clamp received in the clamp-receiving means to their open position and holds the arms in the open position.

15. An infusion pump according to claim 14 wherein the clamp-receiving means further comprises walls in the pumping assembly defining a passageway having an open end adapted for releasably receiving the flexible clamp, and the clamp-opening means comprises a wedge mounted on the pumping assembly, the wedge and the walls being movable relative to one another between the operating position, wherein at least a portion of the wedge is positioned between the clamping arms of a flexible clamp received in the passageway to separate and hold the arms in their open position, and the unloading position, wherein the wedge is not opening the clamping arms of a flexible clamp received in the passageway from their closed position so that the lumen of the IV tubing is closed to fluid flow when the IV tubing is removed from the pumping assembly.

16. An infusion pump according to claim 15 wherein the walls defining the passageway comprise walls in the releasable holding means, and the releasable holding means is movable between a loading and unloading position, wherein the IV tubing may be loaded into or unloaded from the pumping assembly and the walls and flexible clamp are in their unloading position, and the operating position wherein the walls are moved to the operating position relative to the wedge so that the clamping arms of the flexible clamp are moved to their open position for operation of the pumping assembly.

17. An infusion pump according to claim 16 wherein the clamp-receiving means includes a pivotable arm for releasably retaining the flexible clamp in the passageway when the clamp is inserted the first predetermined distance, the releasable holding means of the pumping assembly including a door having a pivotable projecting portion spring biased to a holding position for pressing or holding the arm against the flexible clamp when the door is moved to a closed position, the projecting portion being movable against the spring bias by the pivotable arm when the clamp is partially inserted in the passageway and the door is closed to prevent jamming of the door when the clamp is only partially inserted in the passageway.

18. An infusion pump according to claim 16 wherein the releasable holding means of the pumping assembly includes a door having a projecting portion adapted for releasably retaining the flexible clamp in the passageway when the door is moved to a closed position whereby the flexible clamp is held against longitudinal movement by the projecting portion when the wedge separates the clamping arms of the flexible clamp.

19. A flexible clamp for preventing undesired free flow of fluid through IV tubing when the IV tubing is disconnected from an infusion pump regulating fluid flow to a patient, the clamp having a pair of clamping arms defining a variable width slot along which the IV tubing may be moved between a first position wherein the width of the slot is sufficient to permit the clamp to be positioned longitudinally along the IV tubing, and a second position wherein the width of the slot is normally less than the width of the slot at the first position, the clamping arms being resiliently biased to a closed position wherein the IV tubing is squeezed when at the second position to close the lumen to prevent fluid flow, the clamping arms being movable against the bias to an open position wherein the lumen of the IV tubing is allowed to open so that flow through the lumen is permitted, the clamp further comprising a bridging portion defining an inner end of the slot, the clamping arms of the clamp extending outwardly from the bridging portion and terminating in free ends that define the outer end of the slot, the clamping arms and bridging portion being formed of thermoplastic or synthetic resin material and a resilient spring member biasing the clamping arms to their closed position.

20. A flexible clamp according to claim 19 for use in an infusion pump including a pumping assembly having a wedge for opening the clamping arms of the flexible arms before operation of the pumping assembly; the free ends of the arms being tapered inwardly toward the slot and bridging portion to guide the wedge into the outer end of the slot between the clamping arms.

21. A flexible clamp according to claim 20 wherein the clamping arms define a portion of the slot generally adjacent the inner end of the slot as the second position having a width normally less than the width of the slot at the first position, and the clamping arms have portions generally adjacent their free ends that define an open area generally adjacent the free ends as the first position wherein the width of the slot is sufficient to permit the clamp to move longitudinally along the IV tubing.

22. A flexible clamp according to claim 21 wherein the clamping arms extend in a longitudinal direction of the clamp and the slot is elongate in the longitudinal direction of the clamp, the clamp further comprising at least one laterally outwardly extending ledge for limiting the distance the flexible clamp can be inserted into the infusion pump to a first predetermined distance, the first and second positions being spaced apart along the slot a second predetermined distance substantially equal to the first predetermined distance.

23. A flexible clamp according to claim 22 wherein the at least one ledge includes two ledges extending laterally outwardly from opposite clamping arms at substantially the same longitudinal position along the arms, the ledges and the free ends of the clamping arms being separated by a longitudinal distance substantially equal to the second predetermined distance that the first and second positions are spaced apart along the slot.

24. A flexible clamp for preventing undesired free flow of fluid through IV tubing when the IV tubing is disconnected from an infusion pump regulating fluid flow to a patient, the clamp having a pair of clamping arms defining a variable width slot along which the IV tubing may be moved between a first position wherein the width of the slot is sufficient to permit the clamp to be positioned longitudinally along the IV tubing, and a second position wherein the width of the slot is normally less than the width of the slot at the first position, the clamping arms being resiliently biased to a closed position wherein the IV tubing is squeezed when at the second position to close the lumen to prevent fluid flow, the clamping arms being movable against the bias to an open position wherein the lumen of the IV tubing is allowed to open so that flow through the lumen is permitted, the clamp being adapted for use in an infusion pump including a pumping assembly having a wedge for opening the clamping arms of the flexible arms before operation of the pumping assembly; the clamp further comprising a bridging portion defining an inner end of the slot, the clamping arms and bridging portion being formed of thermoplastic or synthetic resin material and a resilient spring member biasing the clamping arms to their closed position, the clamping arms of the clamp extending outwardly from the bridging portion and terminating in free ends that define the outer end of the slot, the free ends of the arms being tapered inwardly toward the slot and bridging portion to guide the wedge into the outer end of the slot between the clamping arms; the clamping arms defining a portion of the slot generally adjacent the inner end of the slot as the second position having a width normally less than the width of the slot at the first position, and the clamping arms have portions generally adjacent their free ends that define an open area generally adjacent the free ends as the first position wherein the width of the slot is sufficient to permit the clamp to move longitudinally along the IV tubing.

25. A flexible clamp for preventing undesired free flow of fluid through IV tubing when the IV tubing is disconnected from an infusion pump regulating fluid flow to a patient, the clamp having a pair of clamping arms defining a variable width slot along which the IV tubing may be moved between a first position wherein the width of the slot is sufficient to permit the clamp to be positioned longitudinally along the IV tubing, and a second position wherein the width of the slot is normally less than the width of the slot at the first position, the clamping arms being resiliently biased to a closed position wherein the IV tubing is squeezed when at the second position to close the lumen to prevent fluid flow, the clamping arms being movable against the bias to an open position wherein the lumen of the IV tubing is allowed to open so that flow through the lumen is permitted, the clamp further comprising two bridging portions joining the clamping arms and defining opposite ends of the slot, the bridging portions and/or clamping arms being sufficiently flexible to permit the clamping arms to be moved against the bias to their open position.

26. An IV tubing set adapted for use with an infusion pump of the type comprising a pumping assembly including pumping means for pumping fluid through IV tubing to regulate fluid flow through the IV tubing, and releasable holding means for holding IV tubing during operation of the pumping assembly, clamp-receiving means on the pumping assembly for releasably receiving a clamp associated with the IV tubing, and releasable clamp-opening wedge mounted on the pumping assembly for moving a clamp to an open position permitting fluid flow through the IV tubing, the clamp-receiving means and clamp-opening wedge being of the type mounted on the infusion pump for movement relative to one another between an unloading position, wherein the clamp-opening wedge does not hold the arms of a flexible clamp received in the clamp-receiving means in their open position, and an operating position, wherein the clamp-opening wedge moves the arms of a flexible clamp received in the clamp-receiving means to their open position and holds the arms in the open position; the IV tubing set comprising:

IV tubing having a lumen through which fluid may be pumped for administration to a patient; and a flexible clamp associated with the IV tubing and being adapted to be inserted in clamp-receiving means before operation of the infusion pump, the flexible clamp having a pair of clamping arms defining a variable width slot along which the IV tubing may be moved between a first position wherein the width of the slot is sufficient to permit the clamp to be positioned longitudinally along the IV tubing, and a second position wherein the width of the slot is normally less than the width at the first position, the clamping arms being resiliently biased to a closed position wherein the IV tubing is squeezed when in the second position to close the lumen to prevent fluid flow, the clamping arms being movable against the bias to an open position wherein the lumen of the IV tubing is allowed to open so that flow through the lumen is permitted such that the clamp-opening wedge of the infusion pump can move the clamping arms to the open position before operation of the infusion pump;

the clamp further comprising a hinged bridging portion defining an inner end of the slot, the clamping arms of the clamp extending outwardly from the hinged bridging portion and terminating in free ends that define the outer end of the slot, the clamping arms and bridging portion being formed of thermoplastic or synthetic resin material and a resilient spring member biasing the clamping arms to their closed position.

27. An IV tubing set according to claim 26 wherein the free ends of the arms are tapered inwardly toward the slot and bridging portion to guide the clamp-opening wedge into the outer end of the slot between the clamping arms.

28. An IV tubing set according to claim 27 wherein the clamping arms define a portion of the slot generally adjacent the inner end of the slot as the second position having a width normally less than the width of the slot at the first position, and the clamping arms have portions generally adjacent their free ends that define an open area generally adjacent the free ends as the first position wherein the width of the slot is sufficient to permit the clamp to move longitudinally along the IV tubing.

29. An IV tubing set adapted for use with an infusion pump of the type comprising a pumping assembly including pumping means for pumping fluid through IV tubing to regulate fluid flow through the IV tubing, and releasable holding means for holding IV tubing during operation of the pumping assembly, clamp-receiving means on the pumping assembly for releasably receiving a clamp associated with the IV tubing, and releasable clamp-opening means for moving a clamp to an open position permitting fluid flow through the IV tubing, the clamp-receiving means and clamp-opening means being of the type mounted on the infusion pump for movement relative to one another between an unloading position, wherein the clamp-opening means does not hold the arms of a flexible clamp received in the clamp-receiving means in their open position, and an operating position, wherein the clamp-opening means moves the arms of a flexible clamp received in the clamp-receiving means to their open position and holds the arms in the open position, the infusion pump being of the type wherein the clamp-opening means comprises a wedge mounted on the pumping assembly for movement relative to the clamp-receiving means between the unloading and operating positions; the IV tubing set comprising:

IV tubing having a lumen through which fluid may be pumped for administration to a patient; and a flexible clamp associated with the IV tubing and being adapted to be inserted in clamp-receiving means before operation of the infusion pump, the flexible clamp having a pair of clamping arms defining a variable width slot along which the IV tubing may be moved between a first position wherein the width of the slot is sufficient to permit the clamp to be positioned longitudinally along the IV tubing, and a second position wherein the width of the slot is normally less than the width at the first position, the clamping arms being resiliently biased to a closed position wherein the IV tubing is squeezed when in the second position to close the lumen to prevent fluid flow, the clamping arms being movable against the bias to an open position wherein the lumen of the IV tubing is allowed to open so that flow through the lumen is permitted such that the clamp-opening means of the infusion pump can move the clamping arms to the open position before operation of the infusion pump;

the clamp further comprising a hinged bridging portion defining an inner end of the slot, the clamping arms of the clamp extending outwardly from the hinged bridging portion and terminating in free ends that define the outer end of the slot, the clamping arms and bridging portion being formed of thermoplastic or synthetic resin material and a resilient spring member biasing the clamping arms to their closed position, the free ends of the arms being tapered inwardly toward the slot and bridging portion to guide the wedge into the outer end of the slot between the clamping arms;

the clamping arms defining a portion of the slot generally adjacent the inner end of the slot as the second position having a width normally less than the width of the slot at the first position, and the clamping arms have portions generally adjacent their free ends that define an open area generally adjacent the free ends as the first position wherein the width of the slot is sufficient to permit the clamp to move longitudinally along the TV tubing.

30. An IV tubing set according to claim 29 wherein the clamping arms extend in a longitudinal direction of the clamp and the slot is elongate in the longitudinal direction of the clamp, the clamp further comprising at least one laterally outwardly extending ledge for limiting the distance the flexible clamp can be inserted into the clamp-receiving means of the infusion pump to a first predetermined distance, the first and second positions being spaced apart along the slot a second predetermined distance substantially equal to the first predetermined distance.

31. An IV tubing set according to claim 30 wherein the at least one ledge includes two ledges extending laterally outwardly from opposite clamping arms at substantially the same longitudinal position along the arms, the ledges and the free ends of the clamping arms being separated by a longitudinal distance substantially equal to the second predetermined distance that the first and second positions are spaced apart along the slot.

32. An IV tubing set according to claim 31 wherein the IV tubing includes a pumping cassette having flexible walls defining fluid pumping chambers that may be compressed by the pumping means to regulate fluid flow through the IV tubing.

33. An IV tubing set adapted for use with an infusion pump of the type comprising a pumping assembly including pumping means for pumping fluid through IV tubing to regulate fluid flow through the IV tubing, and releasable holding means for holding IV tubing during operation of the pumping assembly, clamp-receiving means on the pumping assembly for releasably receiving a clamp associated with the IV tubing, and releasable clamp-opening means for moving a clamp to an open position permitting fluid flow through the IV tubing, the clamp-receiving means and clamp-opening means being of the type mounted on the infusion pump for movement relative to one another between an unloading position, wherein the clamp-opening means does not hold the arms of a flexible clamp received in the clamp-receiving means in their open position, and an operating position, wherein the clamp-opening means moves the arms of a flexible clamp received in the clamp-receiving means to their open position and holds the arms in the open position; the IV tubing set comprising:

IV tubing having a lumen through which fluid may be pumped for administration to a patient; and a flexible clamp associated with the IV tubing and being adapted to be inserted in clamp-receiving means before operation of the infusion pump, the flexible clamp having a pair of clamping arms defining a variable width slot along which the IV tubing may be moved between a first position wherein the width of the slot is sufficient to permit the clamp to be positioned longitudinally along the IV tubing, and a second position wherein the width of the slot is normally less than the width at the first position, the clamping arms being resiliently biased to a closed position wherein the IV tubing is squeezed when in the second position to close the lumen to prevent fluid flow, the clamping arms being movable against the bias to an open position wherein the lumen of the IV tubing is allowed to open so that flow through the lumen is permitted such that the clamp-opening means of the infusion pump can move the clamping arms to the open position before operation of the infusion pump;

the flexible clamp further comprising two bridging portions joining the clamping arms and defining opposite ends of the slot, the bridging portions and/or clamping arms being sufficiently flexible to permit the clamping arms to be moved against the bias to their open position.

34. An IV tubing set adapted for use with an infusion pump of the type comprising a pumping assembly including pumping means for pumping fluid through IV tubing to regulate fluid flow through the IV tubing, and releasable holding means for holding IV tubing during operation of the pumping assembly, clamp-receiving means on the pumping assembly for releasably receiving a clamp associated with the IV tubing, and releasable clamp-opening means for moving a clamp to an open position permitting fluid flow through the IV tubing, the clamp-receiving means and clamp-opening means being of the type mounted on the infusion pump for movement relative to one another between an unloading position, wherein the clamp-opening means does not hold the arms of a flexible clamp received in the clamp-receiving means in their open position, and an operating position, wherein the clamp-opening means moves the arms of a flexible clamp received in the clamp-receiving means to their open position and holds the arms in the open position; the IV tubing set comprising:

- IV tubing having a lumen through which fluid may be pumped for administration to a patient; and
- a flexible clamp associated with the IV tubing and being adapted to be inserted in clamp-receiving means before operation of the infusion pump, the flexible clamp having a pair of clamping arms extending in a longitudinal direction and defining a variable width slot that is elongate in the longitudinal direction of the clamp and along which the IV tubing may be moved between a first position wherein the width of the slot is sufficient to permit the clamp to be positioned longitudinally along the IV tubing, and a second position wherein the width of the slot is normally less than the width at the first position, the clamping arms being resiliently biased to a closed position wherein the IV tubing is squeezed when in the second position to close the lumen to prevent fluid flow, the clamping arms being movable against the bias to an open position wherein the lumen of the IV tubing is allowed to open so that flow through the lumen is permitted such that the clamp-opening means of the infusion pump can move the clamping arms to the open position before operation of the infusion pump;

the clamp further comprising means for limiting the distance the flexible clamp can be inserted into the clamp-receiving means of the infusion pump to a first predetermined distance, the first and second positions being spaced apart along the slot a second predetermined distance substantially equal to the first predetermined distance.

35. An IV tubing set according to claim 34 wherein the means for limiting the distance the flexible clamp can be inserted into the clamp-receiving means of the infusion pump to the first predetermined distance comprises two ledges extending laterally outwardly from opposite sides of the flexible clamp at substantially the same longitudinal position along the clamp for limiting the distance the clamp can be inserted into the clamp-receiving means of the infusion pump to the first predetermined distance.

36. An IV tubing set according to claim 34 wherein the flexible clamp is formed of thermoplastic or synthetic resin material and a resilient spring member biasing the clamping arms to their closed position.

* * * * *